United States Patent [19]
Juusola

[11] 3,983,745
[45] Oct. 5, 1976

[54] TEST SPECIMEN CRACK CORRELATOR

[75] Inventor: William D. Juusola, Maple Plain, Minn.

[73] Assignee: MTS Systems Corporation, Eden Prairie, Minn.

[22] Filed: Aug. 8, 1975

[21] Appl. No.: 603,135

[52] U.S. Cl. .................................................... 73/91
[51] Int. Cl.² ........................................... G01N 3/36
[58] Field of Search ................. 73/88 R, 91, 97, 95, 73/89

[56] References Cited
UNITED STATES PATENTS

| | | |
|---|---|---|
| 3,087,148 | 4/1963 | Ludewig, Jr. ..................... 73/88 X |
| 3,803,906 | 4/1974 | Ross .............................. 73/88 R X |
| 3,908,447 | 9/1975 | Salt .................................... 73/91 |

*Primary Examiner*—Jerry W. Myracle
*Attorney, Agent, or Firm*—Dugger, Johnson & Westman

[57] ABSTRACT

A testing apparatus for cyclically loading specimens of a known configuration to determine properties of materials from propagation or growth of a crack through the specimen including means to provide a direct output which is a function of crack length derived from measurements of the load and the displacement of the specimen.

18 Claims, 7 Drawing Figures

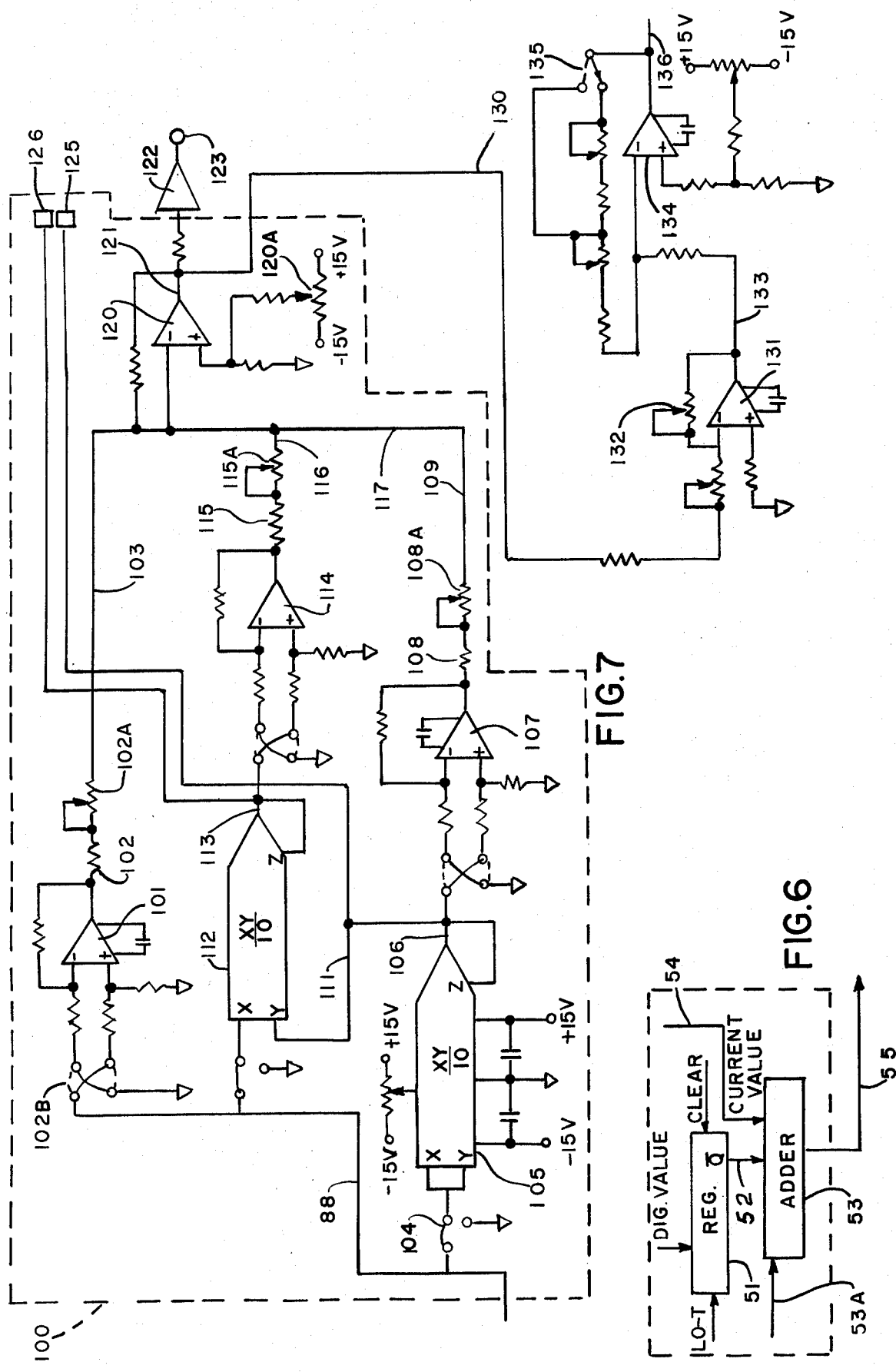

TEST SPECIMEN CRACK CORRELATOR

BACKGROUND OF THE INVENTION

1. Field of the Invention

The present invention relates to devices for directly deriving functions of the length of a crack in a test specimen.

2. Prior Art

Testing of various specimens through the use of servo control systems is well known in the art. Examples of such test systems include U.S. Pat. Nos. 3,751,994, 3,546,931 and 3,375,708. In addition, in certain tests a standard test specimen of known dimensions has been loaded cyclically until a crack develops, and then information concerning the material from which the specimen is derived by noting characteristics associated with growth of the crack length in relation to load on the specimen and displacement of the specimen. The American Society for Testing Materials has provided analytical curves for standard specimens defining the relationship between the crack length divided by its width and a compliance factor of the specimen comprising a quantity proportional to the displacement of the specimen divided by the applied load. These curves are obtained from theoretical elasticity solutions or from finite element approximations. It also has been known that these curves may be defined by equations based on the third order of the compliance factor, and thus functions of the crack length have been separately calculated from measurements of displacement and load on the test specimen.

However, many problems have been encountered in attempts to do this on a continuous basis, utilizing electrical signals to provide the necessary output information. One problem has come from the attempt to determine the compliance of the specimen by attempting to measure the peak to peak loads and peak to peak displacements on the specimen during operation. In loading specimens of this type in a cyclic manner, as the specimen starts to crack the displacement will not always return to zero, and inaccuracies will therefore result. Further, a determination of when the peak (maximum) load is reached requires special techniques to assure accuracy.

Thus, while the desirability of providing an electrical output proportional to the desired parameters has long been known and has been recognized by researchers working in the testing field, the means for deriving such an output has escaped people working in the field until the present invention.

The prior art includes cumulative fatigue life indicators as shown in U.S. Pat. No. 3,777,555, and devices to sense upper and lower end limits as shown in U.S. Pat. No. 3,714,821. A test device providing stress-strain read out is disclosed in U.S. Pat. No. 3,826,902. U.S. Pat. No. 3,744,300 discloses apparatus for determining fatigue and random mechanical loads may be applied to a specimen with the circuit disclosed in U.S. Pat. No. 3,597,967. A method of measuring stress by determining displacement is shown in U.S. Pat. No. 3,071,963.

It is believed that none of these patents mentioned as prior art teach ways of providing a direct reading proportional to the length of a crack in a tension specimen.

SUMMARY OF THE INVENTION

The present invention relates to means for analyzing crack growth in standard specimens and delivering outputs that provide the necessary information for material analysis. Crack growth may be determined directly without separate calculations after obtaining information concerning load on and displacement of the specimen.

The device as shown includes means for cyclicly loading a standard specimen in tension between a maximum and a minimum load, and includes known devices for measuring the load and the displacement of the specimen. The displacement repesents the gap or opening at one edge of the speciment because of a crack that is developing in the specimen.

The test device uses analog inputs comprising voltages representing the load and the displacement, and includes means to convert the analog inputs to digital form for arithmetic calculation relating to the compliance of the specimen, which is a function of the displacement divided by the load applied. After arithmetic computation the digital signal is converted back to analog form for further processing.

An analog computational circuit which provides an output proportional to a third order equation is used to process the compliance signal. Output from this computational circuit provides a signal proportional to the length of the crack divided by the width of the specimen.

The device greatly reduces the length of time necessary to complete analysis of materials used in standard specimens that are provided for studying crack growth rate and other aspects of specimen testing utilizing specimen cracks for deriving the information.

BRIEF DESCRIPTION OF THE DRAWINGS

FIG. 6 is a schematic representation of a typical subtractor used in the circuit of FIG. 5; and FIG. 7 is a schematic representation of analog computational circuitry required for providing an output corresponding to the curve shown in FIG. 3.

DESCRIPTION OF THE PREFERRED EMBODIMENT

Figure 1:
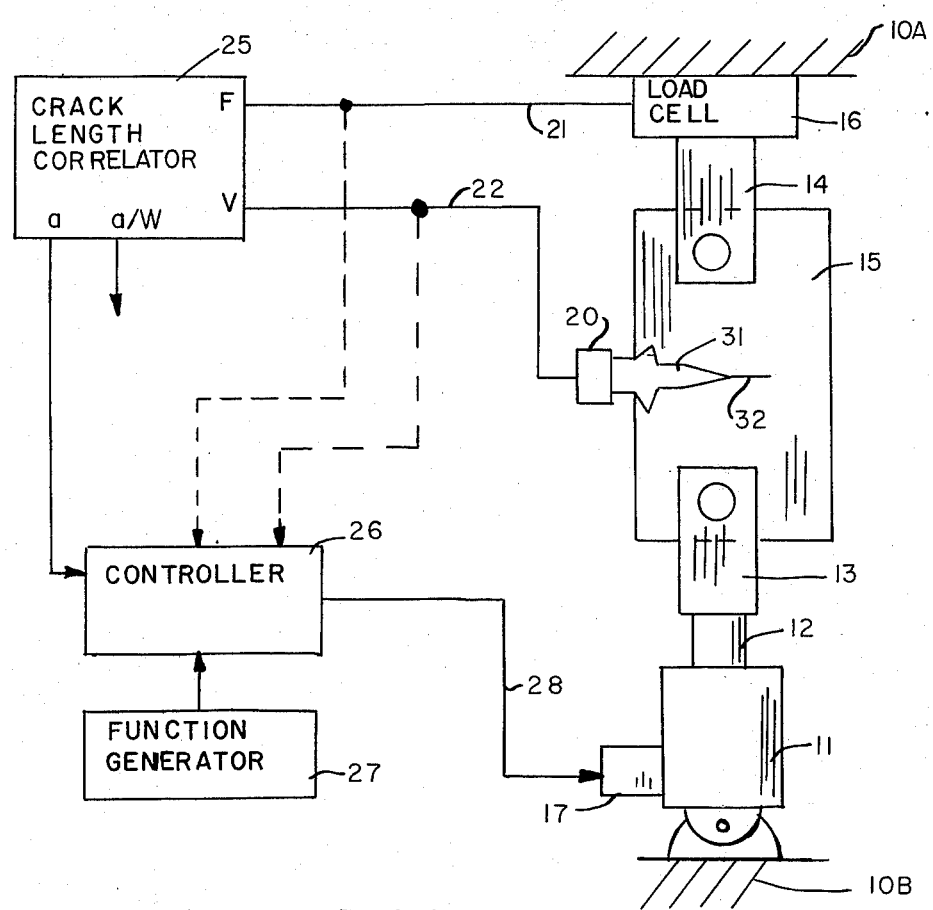
FIG. 1 is a schematic representation of a simplified servo control circuit for testing standard specimens and utilizing the devices of the present invention.

Referring first to FIG. 1, a simplified schematic representation of a typical servo control testing apparatus is shown. A test frame indicated schematically at 10A and 10B mounts an actuator 11 that has a actuable rod 12, and a specimen adapter 13 is used for connecting the actuator to a standard test specimen indicated generally at 15. The frame portion 10A is used for mounting a second specimen adapter 14 through a load cell 16. The actuator 11 shown is a reciprocating hydraulic actuator that is controlled through a servo valve indicated generally at 17 in a normal manner.

The specimen 15 as shown is a standard ASTM compact tension specimen of a known geometrical configuration although the use of this technique is not limited to only this geometry. The specimen is used for testing crack growth in materials. The crack growth is determined by measuring the displacement of the specimen by use of a displacement gage or extensometer 20, which provides an output representing the elongation of the specimen under load.

An electrical output comprising an analog voltage is delivered from the load cell 16 along a line 21, and the analog electrical output from the displacement gage 20 is provided on line 22. The voltage which is proportional to the displacement is represented by the letter "V" and this indicates the amount of the width of the gap caused by a crack in the specimen. The voltage or signal representing load exerted on the specimen is represented by the letter F in the specification.

The analog voltages from lines 21 and 22, F and V, are fed into a crack length correlator circuit indicated generally at 25 which comprises circuitry that provides the necessary outputs for analysis of the specimen and which provides an output $a$ representing specimen crack length that may be used for a feedback signal to control the actuator as a function of crack length. The voltages from either the load cell or the displacement gage may optionally be used as feedback signals if desired. The feedback signal is provided to a servo controller indicated at 26 of usual design which also receives an input from a function generator 27 that provides a desired voltage configuration for controlling the servo valve. The feedback signal used can be compared in the controller with the function generator output to provide an output command signal along line 28 to the servo valve 17 for providing closed loop actuator control.

Closed loop servo controls of this general type are well known in the art and thus the showing in FIG. 1 is merely for orientation and background purposes.

The apparatus just described is used for studying the growth of cracks in standard test specimens. The crack length correlator provides a continuous analog output proportional to crack length and also may be used for providing an indication of stress intensity at the edge of the crack, as more fully explained in the copending application of Patrick J. Cain, for Specimen Crack Stress Intensity Control Loop For Test Device, Ser. No. 603,134, Filed Aug. 8, 1975. Crack growth rate can be obtained easily from an output that provides crack length directly and using a cycle count output pulse to drive an event marker such as recorder. The analog crack length signal enables a research worker to provide new control techniques, and by using computer control devices the command signals that are generated by the function generator may be changed as the crack length changes.

Fracture toughness tests used to evaluate material toughness also can be run on the present device. The output signal of effective crack length that is obtained from the present device provides an efficient means of monitoring the material toughness. The crack length output also can be used for providing a control signal in a closed loop control having a ramped command signal to obtain constant velocity crack propagation in suitable materials if desired.

Figure 2:
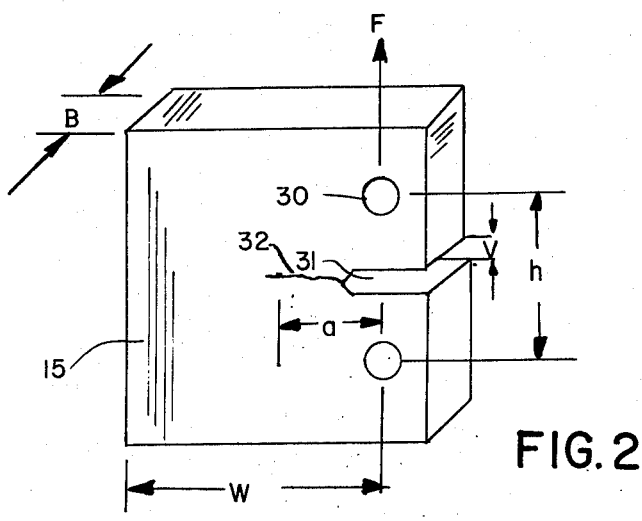
FIG. 2 is a perspective view of a typical standard test specimen illustrating the dimensional information utilized in analyzing or correlating the crack generated in the specimen.

Referring now to FIG. 2, a standard specimen configuration is illustrated. The specimen 15, as shown, is a standard specimen of the American Society for Testing Materials, and can be made of any type of material that is to be tested. It is called a compact tension specimen, and will be referred to as such in this specification. The specimen comprises a block of material having a thickness represented at B, a pair of attachment holes indicated at 30,30 for use with the specimen adapters, a machined gap 31 from which a crack indicated at 32 will grow during testing, and this gap has a width indicated at V, which is the displacement of the specimen. The gap at rest can be equal to zero displacement during testing. In addition, the specimen width is indicated at W in FIG. 2, and comprises the distance from the edge of the specimen opposite the edge having the gap to the center line of the attachment holes is $h$. The crack length is measured from the center of the attachment openings 30 to the end of the crack and is represented by $a$. The tensile force is indicated at F in FIG. 2. In addition in analyzing a specimen it is necessary to use Young's Modulus (the modulus of Elasticity) represented in this specification by E.

It has long been known in testing standard compact tension specimens that the deflection can be measured between any points on the specimen, but generally measuring the crack opening displacement is the most sensitive to changes in crack length. It is desired to know the value of the function $a/W$, which is the crack length divided by the specimen width, and is an output proportional to crack length.

Figure 3:
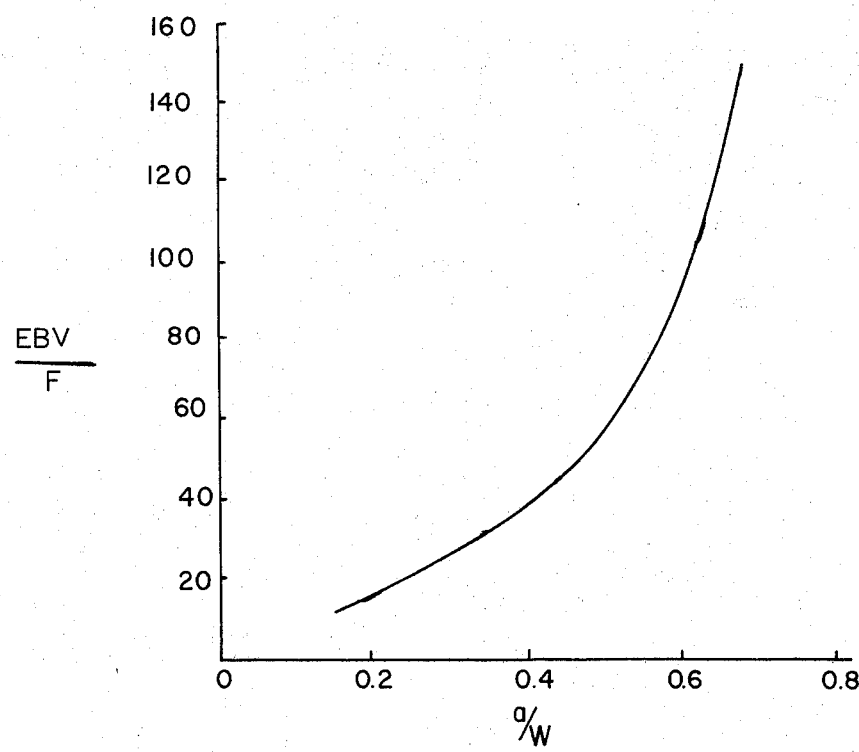
FIG. 3 is a plot of a compliance factor versus the crack length divided by the specimen width for an ASTM standard compact tension specimen shown in FIG. 2.

Also, it has been known that the compliance of the specimen which is a function V/F (displacement divided by load) is important, and can be expressed as a nondimensional parameter including the thickness of the specimen and Young's Modulus as EBV/F. The relationship between the function $a/W$ and the compliance factor can be determined from analysis available for standard test specimen configurations, or from calibration tests. Curves representing this relationship may be obtained from theoretical elasticity solutions, or finite element approximations. In calibration tests, compliance is measured for a specimen with an artificial crack simulated by machined slots. FIG. 3 shows a typical calibration curve that is derived for a ASTM (American Society For Testing Materials) compact tension specimen. This curve is approximated by a polynomial curve $$a/W = A_3 \left(\frac{EBV}{F}\right)^3 + A_2 \left(\frac{EBV}{F}\right)^2 + A_1 \left(\frac{EBV}{F}\right) + A_0 \qquad (1)$$

where the values of $A_0$, $A_1$, $A_2$ and $A_3$ are unique to the specimen geometry.

This information can be derived for any specimen geometry, and this polynomial may be called a "fit function" where the compliance factor may be compared to the a/W function and electrical analog outputs can be provided in accordance with the curve. As long as the plot of EBV/F versus a/W which is a polynominal function of the compliance factor EBV/F can be determined, the specimen geometry can be any desired configuration.

Signals representing V, displacement, and F, force, can be accurately provided by analog voltages with existing load cells and displacement gages or extensometers. In previous devices attempts have been made to measure peak to peak load on the specimen, and also peak to peak displacement, and using these values for determining specimen compliance V/F. Because the displacement at minimum load shifts somewhat as crack length changes, inaccuracies have been introduced.

Figure 4:
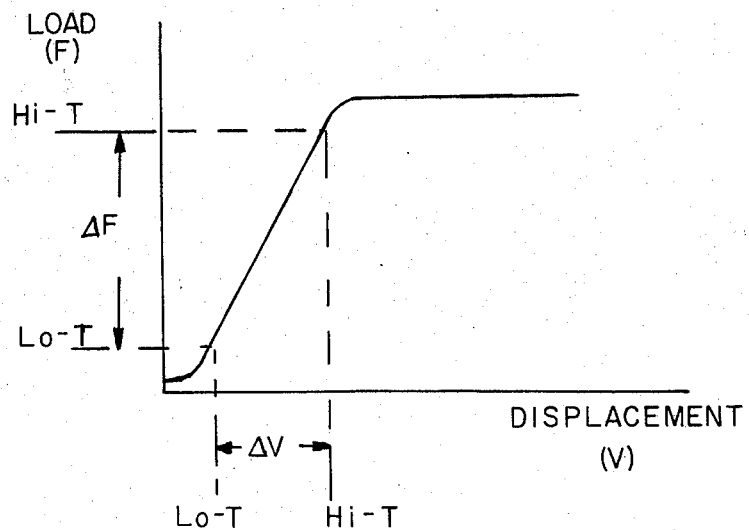
FIG. 4 is a graphic showing of a typical load versus displacement curve on a specimen being tested in the device of FIG. 1.

The present invention includes the concept of providing means for determining the slope of the load versus displacement plot, which is V/F, without the necessity for determining peak loads or peak displacements. This is accomplished by determining two values (low and high) along the linear portion of the loading cycle, subtracting the low values from the high values for each of the load and displacement and then dividing the displacement by the load to obtain the V/F quantity. Reference is made to FIG. 4. Threshold detectors can be used to detect when a voltage exceeds a particular level. Thus, a low threshold of either the load or displacement is detected at some point along the curve represented in FIG. 4, for example the area marked low threshold (Lo-T) and then the second point along the load curve is detected at a high threshold (Hi-T) value. Thus for the load function F, the low threshold is subtracted from the high threshold giving a quantity represented in FIG. 4 as $\Delta F$. For displacement, the value at low threshold is also subtracted from the value at high threshold providing a quantity represented at $\Delta V$ in FIG. 4. The subtracted quantity $\Delta V$ is then divided by the subtracted quantity $\Delta F$ as represented in FIG. 4. This is the function V/F representing the slope of the force versus load curve.

Figure 5:
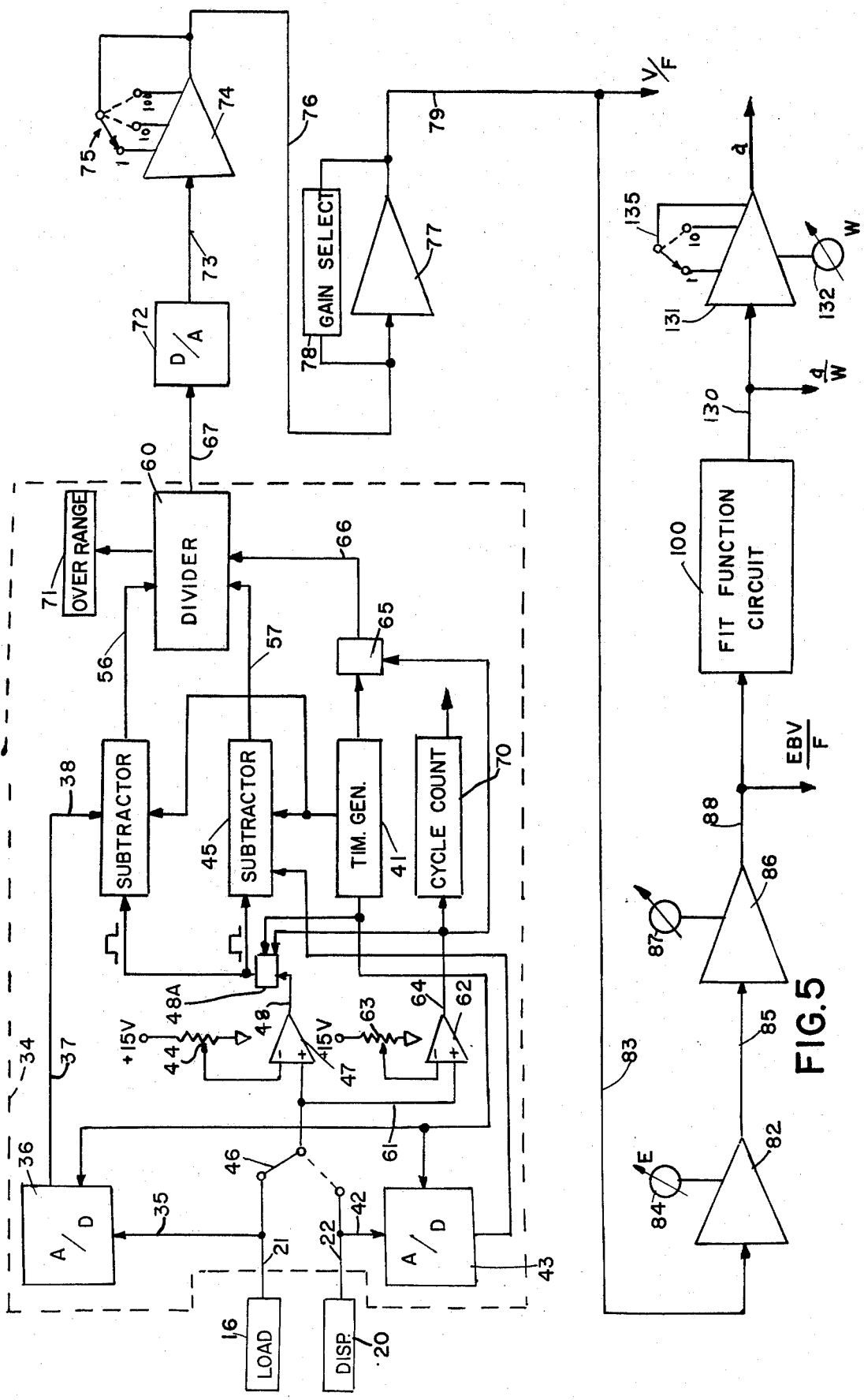
FIG. 5 is a simplified schematic representation of a crack length correlator circuitry used for determining parameters desired in the testing of standard specimens.

Referring now to FIG. 5 it is first assumed that a suitable power supply for providing the necessary reference voltages for operating digital equipment as well as for powering the load cell and displacement gage is used. Such power supplies are well known in the art. The crack correlator circuit 25 shown in FIG. 5 receives analog voltages along lines 21 and 22. These analog voltages are provided to a digital section indicated in dotted lines at 34 for arithmetic computations, and then the digital output is converted back into analog form for further use in the system. Thus, the test system comprising analog input, digital computation, analog output to increase accuracy in computations and to simplify the operational aspects.

The analog voltage representing the load, along line 21 is also provided along line 35 to an analog to digital converter 36. The digital output comprising in this instance a ten bit word representing the analog value is provided along data path 37. The line represented in the digital section 34 do not represent single wires, but rather may represent a plurality of wires carrying the digital information, with as many individual bit paths for each of the data words as is required. Line 37 carries ten bits to a subtractor indicated generally at 38. The analog to digital converter 36 converts values of load to digital form at a desired frequency and is synchronized with the other digital devices with a timing generator indicated at 41 that provides pulses for A/D conversion and for timing various actions, and synchronizing the operation of the digital components in a known manner. These timing pulses can be in several forms and of different duration related to other pulses in any desired manner for achieving the necessary timing.

The analog voltage along line 22 is similarly fed along a line 42 to an analog to digital converter 43 which converts the displacement value into digital form at desired times and transmits this digital representation comprising a ten bit word along a data path or line 44 to a second subtractor 45 used for deriving the digital information concerning displacement.

A switch indicated generally at 46 is used for selecting either the load or displacement information on line 21 or 22 for use in determining the controlling low and high threshold values. Assuming that the load thresholds are to be used, the switch 46 is set as shown, and the analog value from line 21 is fed into one input of a comparator amplifier 47. The other input of the amplifier is connected to an adjustable potentiometer 48 leading from a voltage source so that the amplifier provides an output only when the value on line 21 exceeds a certain set but adjustable amount. The output on line 48 comprises the low threshold signal, and is supplied to logic circuitry 48A which insures the signal is proper and occurs after the start of a loading cycle determined in part by timing signals and alos by signals indicating a previous cycle has been completed. The output signal from logic circuitry 48A which indicates the the selected low threshold is exceeded, is provided to both subtractors 38 and 45.

Referring now specifically to FIG. 6, a typical subtractor for either load or displacement is shown in block diagram to indicate the function in somewhat greater detail. It should be noted that any standard digital subtractor may be used. As shown the subtractors each include a register indicated at 51 and an adder indicated at 53. The register's output is inverted and applied to the adder along with a digital one applied to the least significant carry input shown schematically at 53A. This accomplishes a two's complement type subtractor. When a low threshold signal is received at the input to the register 51 as represented in FIG. 6, the register is clocked and provides an output value that is the inversion of the input value. This value is held by the register and applied along data path 52 to the adder. The other input to the adder is supplied along data path 54 and is the current data value of load or displacement. Therefore the output of the adder is the current value of load or displacement minus the low threshold value of load or displacement.

As stated the register 51 holds the low threshold value and provides this value along the line 52 until the register is clocked again for the next low threshold of the next loading cycle. This simplified showing of the subtractor therefore indicates that after reaching the low threshold in a loading cycle each time the timing generator initiates the converters 36 and 43 to provide a digital output along the lines 37 and 44, there is an effective output from the subtractors that subtracts the low threshold quantity (after it has been exceeded) from the current output of the respective analog to digital converters 36 and 43.

These quantities are supplied along data paths 56 and 57 as ten bit values, to a digital divider indicated at 60. The divider can be of any conventional binary divider construction that provides an output or quotient quantity representing the value of the dividend along data path 56 divided by the value of the divisor along data path 57 whenever the divider receives a signal indicating that it should update its output information.

This update or divide signal is provided when the high threshold value has been exceeded. As shown in FIG. 5, the signal carried by line 21, through switch 46 is provided also along a line 61 connected to one input of a comparator 62 comprising an amplifier. A second input is connected to a potentiometer 63 leading from a voltage source. The output along line 64 is supplied to each of the subtractors only after the value on line 61 exceeds a preset adjustable amount as set by the potentiometer 63. When the high threshold is reached, a pulse is provided through appropriate circuits from the output of amplifier 62 and this is coordinated with the timing generator output through suitable logic connections indicated generally by a box 65 to provide an update signal along data path 66 to the divider 60 to tell it to divide and provide a new quotient along an output data path 67 of the divider. The logic devices indicated at 65 include suitable gates to insure that the updata signal along path 66 is provided only at the proper clock time from the timing generator and after desired happenings have occurred, such as after a low threshold signal has been exceeded in the respective registers of the subtractors. In some instances where continually updated output information is desired from the divider, the divider can be controlled by the timing generator to provide an output quotient each time the analog to digital converters 36 to 43 convert.

Additionally, the output from the amplifier 62 can be used as a signal to logic circuitry 48A to indicate the desired high threshold has been exceeded (to be used for resetting the subtractors at a subsequent clock pulse), and it can be used to provide a cycle count pulse to a cycle count circuit indicated generally at 70, so that each time the specimen is loaded, and relaxed, a count is kept of the number of cycles on the specimen.

The divider 60 can have an overrange indicator 71 of usual design to indicate when it is not functional, and this is also well known in the art. The data word representing the quotient obtained when the data along path 56 is divided by the data along path 57, in the form shown, comprises a twelve bit word fed along the path or line 67 to a digital to analog converter 72. The output of the digital to analog converter 72 comprises an analog voltage along line 73 which is proportional to V/F, and is a measure of the compliance of the test specimen.

It is to be noted that the connections for the threshold detectors have been greatly simplified and do not include the power connections for the amplifiers and other components that are used with the amplifiers. Amplifiers 47 and 62 can be type 311N amplifiers operating from a power supply providing plus and minus 15 volts. The digital pulses provided are generally in the range of 5 volts above a common digital ground, as is common in digital techniques.

In order to take the raw value from the digital to analog converter 72 and provide useful output signals with a maximum range of 10 volts, as is desired, it is necessary to have range selectors that provide factors or constants to bring the raw signal within the desired range for any particular material. Such an amplifier is shown at 74 connected to line 73, and provides a scaling factor through a load range switch 75 to make the output along the line 76 in the proper range whether metal or plastics are being used for the material in the specimen. The selection depends on the force and displacement characteristics of the specimen. Additionally, the line 76 is connected through an amplifier 77 that includes suitable selectable resistors indicated at 78 for providing different gains for displacement and load ranges that may be necessary to obtain a satisfactory level of analog voltage representing V/F along the line 79. The signal V/F may therefore be used directly by providing a terminal on the line 79. It can be used directly for plotting a curve on a recorder, or the value can be used for external calculations.

However, in order to obtain a desired value of $a/W$ or just $a$, comprising the crack length, it is necessary to add constant factors for Young's Modulus, and the thickness of the specimen. This is done by using an amplifier 82 connected through a line 83 to a line 79, and providing an adjustable gain indicated at 84 in the usual manner so that the output along line 85 is V/F multiplied by E, the value that is added in amplifier 82. Then line 85 in turn is connected to an amplifier 86 that has an adjustable gain device 87 that provides a constant factor representative of the width B of the specimen, so that the output along the line 88 is EBV/F comprising a nondimensional compliance factor of the specimen.

The information on line 88 can be taken directly for use as a compliance factor if desired. However, as was previously explained one of the functions that is desired to be known in testing these specimens is the crack length, ($a$) and the ratio of the crack length to the specimen width, ($a/W$). As shown in FIG. 3, the curve representing the relationship between EBV/F and $a/W$ can be empirically determined in accordance with the equation previously given. FIG. 7 shows the circuitry for providing an output from a fit function circuit indicated generally at 100. In FIG. 7 the multiplication circuits illustrated are commercially available circuits that are connected together and the constants required in the equation are added in in accordance with electrical outputs to obtain the desired level of output. For example setting EBV/F equal to $y$, in equation (1) above, for the specimen shown with $h/W$ equal to 0.6 the fit function equation in terms of volts is:

$$a/W = 0.02726y^3 - 0.468y^2 + 2.897y - 0.043$$

Line 88, which contains the value of the function EBV/F is provided to a selected input of an amplifier 101, whose other input is connected to provide a desired gain. The amplifiers in this circuit may be type 301AN amplifiers. The connection can be through a jumper connection 102B so that the inputs can be reversed if desired and the output of the amplifier is fed through a resistor 102 that includes an adjustable portion 102A for adjusting the constant $A_1$ in equation (1) above. This output is then provided along a line 103. This is the first order quantity $A_1$ (EBV/F) of the equation given at (1).

The line 88 is also connected through jumper connections 104 to a multiplication circuit 105 that is a standard circuit No. 4202B sold by Burr Brown Research Corporation, Tucson, Ariz. These multiplication circuits include balance connections and power connections which are shown for purposes of illustration with circuit 105 but are eliminated at the other showing of this type of circuit. As shown, the quantity from line 88 is fed into both the $x$ and $y$ inputs of multiplication circuit 105. The output of the circuit is $xy/10$, and therefore is proportional to the square of the quantity EBV/F. The output along line 106 is fed through jumper connection to a suitable amplifier 107, to provide a signal of usable level and the value for the constant $A_2$ is added through resistors 108, including an adjustable portion 108A, selected to provide the desired level for this coefficient. This output $A_2$ EBV/F from equation (1) is also fed along the line 109.

The squared quantity of the polynominal equation is connected through a line 111 to an input of a multiplication circuit 112. Line 88 is connected to the other input of the multiplication circuit 112 through jumper connections, and thus the output along line 113 is equal to the quantity EBV/F cubed. The line 103 is connected through suitable jumper connections for polarity purposes to an amplifier 114, and through a resistor 115 having an adjustable portion 115A for providing the constant $A_3$. The quantity $A_3$ (EBV/F) from equation (1) is thus provided on line 116.

The lines 103, 116 and 109 are summed together on a line 117 and fed into one input of an amplifier 120. The other input of amplifier 120 is connected to an input circuit 120A providing an adjustable function added to the summed quantity on line 117. This adjustable quantity is the $A_0$ constant from equation (1). The output along the line 121 from amplifier 120 is a function of $a/W$ and is passed through an amplifier 122. The output of the amplifier has the $a/W$ term scaled to a desired level. This $a/W$ signal is proportional to the values of $a/W$ that would be calculated in accordance with the curve shown in FIG. 3, for varying values of the quantity EBV/F.

It should also be noted that the squared term, $(EBV/F)^2$ of the equation is provided at the terminal 125 for use in other manners if desired, and the cubed term, $(EBV/F)^3$ can be provided at a terminal 126 for external use as well. These terms may be used in the circuitry shown in the previously mentioned application of Patrick J. Cain, Ser. No. 603,134, filed Aug. 8, 1975.

The analog voltage at terminal 123 representing $a/W$ is useful in direct analysis, and can be used for driving recorders, or for other information such as visual display.

Further, the actual crack length $a$ is of interest, and can be provided by using the output of line 121 which is proportional to $a/W$, and connecting a line 130 to receive the quantity, which is fed into an amplifier 131 that has an adjustable input 132 for adding a value equal to the constant W and thereby multiplying the quantity on line 130 by the quantity W to provide an output equal to the crack length $a$. This output along line 133 can be passed through a further amplifier 134 that has a scaling selection switch 135 for obtaining the proper scaling so that an output along line 136 is at the proper range for use and does represent the value of crack length in a usable range.

The connections for the amplifiers 131 and 134 are shown in detail here, to exemplify the type of connections that can be used on the other amplifiers where scaling multiplication of terms is desired, for example in the amplifiers shown at 74 and 77. Of course the gain selection device 78 would include as many resistors as needed for obtaining the necessary gain under different operating conditions and for different specimens. The quantity representing crack length $a$ also may be used as a feedback signal for controlling the servo system as a function of crack length.

Thus, the device herein provides means for obtaining an output proportional to crack length in a standard tension specimen, which output is useful in analysis of materials.

The ability to provide a fit function from the circuit shown at 100 permits the direct solution of a polynomial equation representing the curve applied of the compliance factor EBP/V versus $a/W$ electrically. The analog voltage can be directly used for determining the material properties.

The analog to digital converters can be of any desired form that provide necessary accuracy and are commercially available. Likewise, the divider shown can be of any desired form of digital divider now presently on the market which will provide a quotient when a suitable digital signal telling the divider to divide is received.

The present system has an analog input and means for digital subtraction and division of the parameters and then converts to analog signals for further processing to provide accuracy and convenience. The use of high and low threshold detection for determining the V/F function eleminates problems with zero shift and plasticity effects.

What is claimed is:

1. A test device for determining crack growth rates in test specimens comprising means for cyclically loading a specimen, first means for determining the load applied to a loaded specimen, second means for determining the displacement of a loaded specimen in a region to measure the size of a crack in such a specimen, said first and second means providing analog signals representing load and displacement, means to convert the analog signals from said first and second means to digital form, means to arithmetically compute in digital form a quantity comprising the displacement value divided by the load value, and means to convert the digital output of said means to compute to an analog signal comprising the output of said test device.

2. The combination as specified in claim 1 and further analog multiplying means to multiply said output by selected factors to provide a correlation of growth of said crack in said specimen.

3. The combination as specified in claim 2 wherein said analog multiplying means includes means to provide adjustable gain for displacement and load ranges of a specimen being loaded, and to multiply the output by a value equal to the Young's modulus for the material from which a tested specimen is made, and by a scaled value representing the thickness of a specimen being tested to provide a second quantity.

4. The combination as specified in claim 3 wherein said analog mutliplying means further includes means to utilize the second quantity to provide an analog output representing a third order equation providing an output from the analog multiplying means which is substantially proportional to the crack length divided by the specimen width.

5. The combination as specified in claim 4 wherein said last mentioned means includes circuitry having a first portion adding a desired gain and an adjustable constant to the analog value of said second quantity, a second portion multiplying said second quantity by itself to provide a signal representing the square of the second quantity, and to multiply said signal representing the square by a constant, and a third portion multiplying the square of the second quantity by the second quantity to provide a signal representing the cube of the second quantity and multiplying the signal representing the cube by a third constant, means to sum the outputs of said first, second and third portions, and means to provide a fourth constant to the summed signals to provide said analog value substantially proportional to crack length divided by specimen width.

6. The combination as specified in claim 1 wherein one of said first and second means is connected to means for providing a first signal when the output of said one means connected exceeds a first preselected level and is also connected to separate means to provide a second signal when the output of said one means exceeds a second preselected level higher than the first level.

7. The combination as specified in claim 6 wherein said means to arithmetically compute includes subtractor means receiving the digital values of the outputs of said first and second means, said subtractor means being connected to the output of said means to provide the first signal, and including means to hold the digital values of the outputs of the first and second means when the first signal is received by said subtractor means, said subtractor means subsequently receiving periodic digital values of said first and second means and providing an output comprising the difference between the held values and the subsequent values, the outputs of said subtractor means being provided to a divider, and means connecting said means providing the second signal to said divider and causing an output from said divider in response to said second signal.

8. A test apparatus for testing a specimen in which crack growth rates are to be studied, and including means to apply a cyclic tension load to a specimen adjacent one edge thereof, a specimen being tested having a thickness represented by B, and a speciment width represented by W, means to determine the force F applied to a specimen being tested, means to determine the displacement V in a crack area of a specimen being tested, a specimen crack having a length $a$ as it propagates across the width of a specimen under loading by said means to load a specimen, the specimen being tested having a known geometry providing a third order polynomial curve when the quantity EBV/F is plotted versus the quantity $a$/W, where E is Young's modulus for the material from which the specimen is made; the improvement comprising an electronic circuit to provide direct readout of a voltage which is substantially proportional to crack length including means to provide a signal representing the displacement V divided by the force F, (V/F), means to multiply said signal by electrical quantities representative of E and B to provide an output substantially proportional to EBV/F, and a multiplier circuit to receive the separate signal representing the quantity EBV/F including a plurality of portions connected to provide an output signal substantially proportional to a polynomial function of EBV/F which represents the quantity $a$/W.

9. The combination of claim 8 wherein said plurality of portions includes a second portion providing an output $A_2$ (EBV/F)$^2$ and a third portion providing the quantity $A_3$ (EBV/F)$^3$, and means to sum the outputs of said first and second and third portions and add said first, second and third portions to an electrical signal representing $A_0$, to thereby provide an output signal substantially proportional to the quantity $a$/W where $A_0$, $A_1$, $A_2$ and $A_3$ are constants.

10. The combination as specified in claim 8 and means to multiply the last mentioned signal representing $a$/W by an electrical signal proportional to the width of the specimen to provide an analog output representing length of a crack of a specimen being tested.

11. The combination of claim 10 wherein said means to apply a cyclic tension load includes servo control means, and means to connect the analog output representing the length of a crack to the servo control means to function as a feedback signal in the servo control means.

12. The combination as specified in claim 8 wherein the means to provide the signal proportional to the quantity V/F includes first and second means to provide analog signals representing the displacement of a specimen being tested and the load on a specimen being tested, respectively, means to convert said analog signals to digital form, and digital divider means to divide selected values of V by selected values of F.

13. The combination as specified in claim 12 wherein said value of V and the value of F are provided by means detecting a threshold value of said first and second means at a low load point in each operation cycle, and means to subsequently detect a higher value of said first and second means in the same cycle of loading, means to subtract the low values from each of first and second means from the high values of the corresponding means, and means to divide the remainders of the two values in said digital divider.

14. The combination as specified in claim 12 wherein the means to provide the signal proportional to the quantity V/F includes means to convert the output of said divider into analog form.

15. A test device for testing specimens wherein values representing selected test parameters must be arithmetically compared or computed and the comparator is desired as an analog signal comprising means for cyclically loading a specimen, means for determining at least two parameters related to loading of the specimen, said means providing analog output signals representing the parameters, means to convert the analog signals to digital form, means to arithmetically compare the parameters in digital form, means to convert the digital value of the compared parameters to an analog signal comprising the output of said test device.

16. The test device of claim 15 wherein said means to arithmetically compare includes means to divide the digital value of one parameter by another.

17. In a test device for testing specimens and obtaining a signal proportional to the displacement of a specimen divided by the load on a specimen and including means to cyclically load a specimen, and signal means to provide separate signals representing the displacement and the load on a specimen, respectively, the improvement comprising threshold detection means connected to said signal means to provide a first signal indicating when a selected one of said displacement and load signals exceeds a first predetermined amount and to provide a second signal when said selected one signal exceeds a second greater amount in the same cycle of loading, means connected to the threshold detection means and to the signal means to determine different values between the value of said displacement and load signals respectively at the time of said first signal and at the time of said second signal and to divide said difference values, one by the other.

18. The device of claim 17 wherein said signal means provide analog signals, means connected to the signal means to convert said analog signals to digital equivalents, and means to connect said means to convert to said means to determine the difference.

\* \* \* \* \*